(12) United States Patent
Bhagat et al.

(10) Patent No.: US 8,945,214 B2
(45) Date of Patent: Feb. 3, 2015

(54) INTRAVITREAL APPLICATOR

(71) Applicant: Allergan, Inc., Irvine, CA (US)

(72) Inventors: Rahul Bhagat, Irvine, CA (US); Zoran Novakovic, Irvine, CA (US); Shawn Davis, Rancho Santa Margarita, CA (US); David Mucientes, Long Beach, CA (US); Thomas David Reid Ford, Royston (GB); Richard Rhys Mathias, Royston (GB)

(73) Assignee: Allergan, Inc., Irvine, CA (US)

( * ) Notice: Subject to any disclaimer, the term of this patent is extended or adjusted under 35 U.S.C. 154(b) by 231 days.

(21) Appl. No.: 13/718,991

(22) Filed: Dec. 18, 2012

(65) Prior Publication Data

US 2013/0158561 A1 Jun. 20, 2013

Related U.S. Application Data

(60) Provisional application No. 61/577,600, filed on Dec. 19, 2011.

(51) Int. Cl.
*A61F 2/16* (2006.01)
*A61F 2/14* (2006.01)
*A61F 9/00* (2006.01)

(52) U.S. Cl.
CPC .............. *A61F 2/14* (2013.01); *A61F 9/0017* (2013.01)
USPC ........................................ 623/6.12

(58) Field of Classification Search
USPC .......... 623/6.12; 606/107; 604/27, 57, 60, 61, 604/62, 63, 64, 506
See application file for complete search history.

(56) References Cited

U.S. PATENT DOCUMENTS

| | | |
|---|---|---|
| 6,369,116 B1 | 4/2002 | Wong et al. |
| 6,726,918 B1 | 4/2004 | Wong et al. |
| 6,899,717 B2 | 5/2005 | Weber et al. |
| 7,033,605 B2 | 4/2006 | Wong |
| 7,090,681 B2 | 8/2006 | Weber et al. |
| 7,147,644 B2 | 12/2006 | Weber et al. |
| 7,468,065 B2 | 12/2008 | Weber et al. |
| 7,625,582 B2 | 12/2009 | Wong |
| 7,846,468 B2 | 12/2010 | Wong |
| 8,034,366 B2 | 10/2011 | Shiah et al. |
| 8,043,628 B2 | 10/2011 | Wong |
| 8,435,248 B2 * | 5/2013 | Herman .................. 606/107 |
| 2002/0193804 A1* | 12/2002 | Tickle .................... 606/107 |
| 2006/0241650 A1* | 10/2006 | Weber et al. ............. 606/107 |
| 2006/0264971 A1* | 11/2006 | Akahoshi ................. 606/107 |
| 2007/0150055 A1* | 6/2007 | Pynson .................. 623/6.12 |
| 2008/0058830 A1* | 3/2008 | Cole et al. .............. 606/107 |
| 2009/0036827 A1 | 2/2009 | Cazzini |
| 2009/0132040 A1 | 5/2009 | Frion et al. |
| 2009/0292293 A1* | 11/2009 | Bogaert et al. ........... 606/107 |
| 2010/0173866 A1 | 7/2010 | Hee et al. |
| 2011/0137321 A1* | 6/2011 | Pynson .................. 606/107 |
| 2011/0238075 A1* | 9/2011 | Clauson et al. .......... 606/107 |
| 2012/0283741 A1* | 11/2012 | Luloh et al. ............. 606/107 |

FOREIGN PATENT DOCUMENTS

WO  2009/061988  5/2009

* cited by examiner

*Primary Examiner* — Jonathan W Miles
(74) *Attorney, Agent, or Firm* — Linda Allyson Nassif

(57) ABSTRACT

An assembly for implanting ocular implants into a mammalian eye is provided. The assembly generally includes a cannula having a curved distal end, an injector mechanism coupled to the cannula for linearly moving one or more implant segments in the cannula toward the curved distal end, and a rotator mechanism for rotating the cannula about a longitudinal axis thereof.

16 Claims, 5 Drawing Sheets

INTRAVITREAL APPLICATOR

This application claims priority to U.S. Provisional Application No. 61/577,600, filed Dec. 19, 2011, the entire contents of which is incorporated herein by reference.

The present invention generally relates to a device for implanting ocular implants in an eye, and more specifically relates to an intravitreal applicator for ocular implants.

The present invention generally relates to apparatus useful in implanting ocular implants in eyes. More particularly, the invention relates to pre-loaded ocular implant delivery assemblies for delivering, placing, positioning and the like, ocular implants in an eye, for example, at one or more of various locations in an eye, for example, a mammalian eye.

The mammalian eye is a complex organ comprising an outer covering including the sclera (the tough white portion of the exterior of the eye) and the cornea (the clear outer portion covering the pupil and iris). In a medial cross section, from anterior to posterior, the eye comprises features including, without limitation: the cornea, the anterior chamber (a hollow feature filled with a watery, clear fluid called the aqueous humor and bounded by the cornea in the front and the lens in the posterior direction), the iris (a curtain-like feature that can open and close in response to ambient light), the lens, the posterior chamber (filled with a viscous fluid called the vitreous humor), the retina (the innermost coating of the back of the eye and comprising light-sensitive neurons), the choroid (an intermediate layer providing blood vessels to the cells of the eye), and the sclera. The posterior chamber comprises approximately ⅔ of the inner volume of the eye, while the anterior chamber and its associated features (lens, iris etc.) comprise about ⅓ of the eye's inner volume.

Ocular implants containing one or more therapeutic components combined with matrix components, such as polymeric components, have been proposed for use, for example, to treat conditions/diseases of the eye. Such implants have been suggested for use at various locations in the eye, for example, in the vitreous, subconjunctivally, anterior chamber and posterior chamber of the eye.

Although such prior art implants have taken on various shapes, forms and configurations, one very useful implant form is a plurality of variously sized microparticles. For example, intravitreal injection of conventional microparticles, which average about 1-100 microns in size, is known and has been previously practiced. This injection of such microparticles is usually conducted using the microparticles suspended in a liquid aqueous medium.

Another type of implant that has been found to be very useful is in the form of a rod shape. Dry delivery in the eye of extruded, rod shaped implants, for example having diameters of about 450 microns and maximum lengths of 3-6 millimeters, has been successfully accomplished. However, it would be highly desirable to reduce the diameter of the implant in order to allow the use of a narrower gauge needle for injection. Reducing the diameter of such rod shaped implants often reduces the strength of the implant so that it breaks up during handling. Moreover, as such a rod shaped implant is reduced in diameter, the length of the implant gets much longer (so as to deliver an equal amount of therapeutic component to the eye) making the implant impractical for use.

U.S. Pat. Nos. 6,899,717; 7,090,681; 7,468,065; 7,147,644, disclose various devices and assemblies for delivering such ocular implants into eyes. The entire disclosure of each of these documents is incorporated herein by this specific reference.

It would be beneficial to provide improved assemblies for delivering ocular implants into eyes through a needle that is as narrow as possible.

SUMMARY

New ocular implant delivery assemblies have been discovered. The present assemblies are useful in conveniently and controllably placing ocular implants, for example, substantially biodegradable drug delivery ocular implants containing pharmaceutical compositions, into an eye in a single, relatively straightforward procedure without causing any substantial breakage or other damage to the implant. Further, the apparatus enables injection of such implants, for example but not limited to such implants in the form of one or more thin filaments or microparticles, into an eye by means of an exceptionally small cannula or needle, thereby reducing invasiveness of the injection procedure and accelerating healing relative to injection of implants by means of more conventionally sized needles.

In one aspect of the invention, an assembly is provided for implanting ocular implants into a mammalian eye wherein the assembly allows an implant to be delivered in the form of multiple particles or segments, into an eye in a spaced apart manner. The assembly may be in the form of a self-contained, single use, handpiece, easily manipulable by an operator, e.g. physician, without need for batteries or motor.

Advantageously, after positioning the cannula distal tip in a desired target region of the eye, an operator of the device need not reposition the device in order to deliver multiple, separate implant segments. Further, delivery of subsequent segments does not disturb or disrupt the position of prior delivered segments.

Generally, this is achieved by providing a cannula, or needle, having a slightly curved distal end, and providing a mechanism for rotating the cannula, for example, in a stepwise manner, after each segment is delivered into the eye. The rotator mechanism is structured to rotate the cannula in a stepwise manner such that a distal tip of the cannula becomes offset, for example, rotationally offset, relative to a position of the distal tip prior to each rotation step.

More specifically, in one embodiment, multiple implant segments to be delivered to an eye are disposed linearly within the cannula. The assembly comprises an injector mechanism coupled to the cannula for linearly moving the implant segments in the cannula toward the curved distal end and out of an outlet port in or adjacent a distal tip of the cannula. The assembly further comprises a rotator mechanism for rotating the cannula about a longitudinal axis thereof, thereby repositioning the outlet port in a position offset from the position prior to rotation.

The injector mechanism may be structured in any suitable manner so as to enable or cause linear movement of implant segments toward the distal end of the cannula. The rotator mechanism may comprise any suitable mechanism for rotating the cannula within the assembly.

For example, in one embodiment, the injector mechanism comprises a drive rod assembly and a compression spring coupled thereto. The injector mechanism further comprises a plunger having a distal end movable in the cannula. When the device is actuated by the operator, for example, by the operator pressing a release button or other actuating device, the drive rod assembly is driven forward by the compression spring causing the plunger to push the implant segments along the cannula and out of an outlet port in the distal tip of the cannula. In some embodiments, the rotator mechanism is structured to rotate the curved distal end of the cannula in a stepwise manner. Delivery of implant segments may take place between rotation steps.

For example, the rotator mechanism comprises a rotatable sleeve having helical ribs, and a torsion spring for applying a restoring force.

In one aspect of the invention, the cannula has a curvature radius of between about R 20 to about R 80. The distal tip of the cannula may be offset by between about 0.1 mm to about 1.0 mm. In a certain embodiment, the cannula has a curvature of about R 50 and the cannula distal tip is offset by 0.3 mm.

Each and every feature described herein, and each and every combination of two or more of such features, is included within the scope of the present invention provided that the features included in such a combination are not mutually inconsistent.

DETAILED DESCRIPTION

An exemplary embodiment of the invention is shown in the Figures and is described below.

Figure 1:
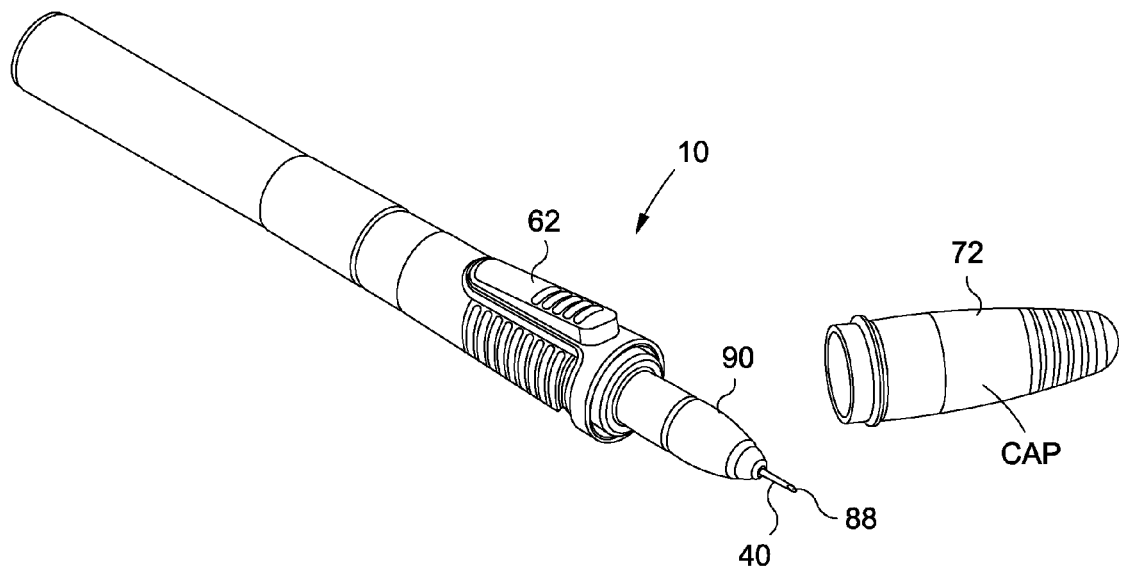
FIG. 1 is a perspective view of a device in accordance with the invention.

The assembly, or device 10, of the invention, shown generally in FIG. 1, can be configured as a single use device, made of simple molded components. The device 10 may be in the form of a self-contained, single use, handpiece, easily manipulable by an operator, e.g. physician, without need for batteries or motor.

Figure 2:
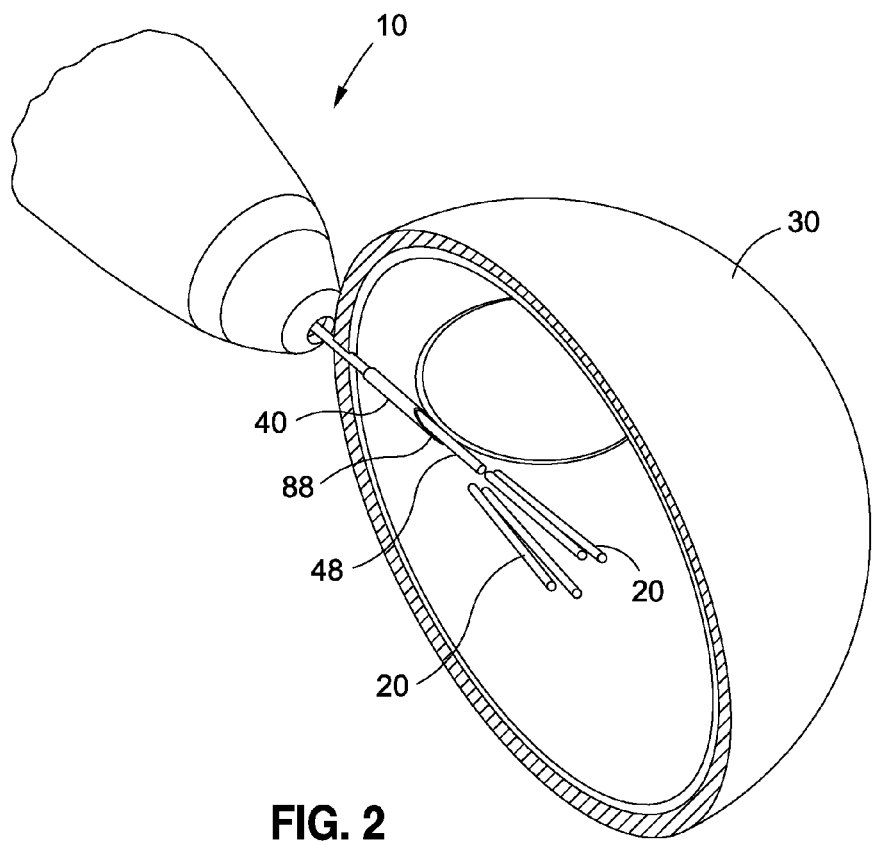
FIG. 2 is a simplified view of the device being used to deliver multiple intraocular implant segments to the eye, using 90 degree rotation steps of the cannula.

Turning as well briefly to FIG. 2, device 10 is structured to be capable of injecting multiple implant segments into the eye 30, for example, the posterior segment of the eye, with sufficient separation such that the implant segments 20 that are injected first are not disturbed by the injection of subsequent segments. Contact between an implant and fragile structures of the eye, such as the retina, can be controlled or avoided.

In other words, the device 10 allows an implant to be delivered in the form of multiple particles or segments, into an eye 30, for example, in a spaced apart manner and, advantageously, using a single insertion of a needle 40.

Advantageously, after positioning the needle or cannula distal tip 88 in a desired target region of the eye 30, an operator of the device need not reposition the device in order to deliver multiple, separate implant segments 20. Further, delivery of subsequent segments 20 does not disturb or disrupt the position of prior delivered segments 20.

Generally, this may be achieved by providing cannula 40, (also interchangeably referred to herein as a needle 40) which has a slightly curved distal end 88, and providing a mechanism for rotating the cannula 40, for example, in a stepwise manner, after each segment 20 is delivered into the eye 30. See briefly, for example, FIG. 6B.

The rotator mechanism is structured to rotate the cannula 40 in a stepwise manner such that a distal tip 88 of the cannula 40 becomes offset, for example, rotationally offset, relative to a position of the distal tip prior to each rotation step.

More specifically, assembly 10 can be used to introduce ocular implants 20, for example, polymeric drug delivery systems, through a cannula, for example, a 22 G, 23 G, 24 G, 25 G, 26 G, 27 G, 28 G or finer needle 40, into the eye 30.

In one aspect of the invention, the cannula or needle 40 has a curvature radius of between about R 20 to about R 80. The distal tip of the cannula may be offset by between about 0.1 mm to about 1.0 mm. In a certain embodiment, the cannula has a curvature of about R 50 and the cannula distal tip is offset by 0.3 mm.

In one embodiment, the assembly 10 comprises a 0.51 mm diameter needle (25 G) 40 which produces a leak-free wound with simple needle insertion technique. The needle 40 has a tip offset by about 0.30 mm.

Using this needle 40 with device 10, four implant segments 20 can be delivered to the eye in a spaced apart relationship, without need to withdraw or reposition the device between delivery of segments 20, as shown in FIG. 2.

More specifically, in one aspect of the invention, a single dose of drug to be delivered is delivered in the form of one or more of plurality of ocular implants, for example, one, two, three, four, five, six or more implant segments 20, into a target region of an eye, for example, a target region of the vitreous. The total implant, comprising the one or more implant segments 20, to be implanted in an eye in a single procedure may be an implant having a total implant length of between about 10 and about 40 mm, for example, between about 20 and about 30 mm. In one embodiment the total implant length is about 24 mm and comprises 4 segments each of about 6 mm in length. It will be appreciated that the assembly 10 can be modified within the scope of the invention to accommodate other implant variants, for example, longer or shorter implants comprising fewer or greater numbers of implant segments.

In one embodiment, the implants 20 are intravitreal implants, such as solid, bioresorbable, or biodegradable, polymeric drug delivery systems (DDS) and/or other intraocular implants, such as, for example, those disclosed in U.S. Pat. Nos. 6,369,116; 6,726,918; 7,033,605; 8,043,628; 7,846,468; 8,034,366; and 7,625,582, the entire disclosure of each of these patents being incorporated herein by this specific reference.

The implant segments 20 may be housed within needle/cannula 40 prior to device actuation.

The implant segments 20 may be injected at a controlled speed such that the distance they are injected into the eye is repeatable. The injection speed is unaffected by the force with which the user operates an actuation mechanism, for example, an activation trigger, button or switch.

Although any suitable mechanism can be employed to accomplish the aims of the present invention, such mechanisms being considered within the scope of the invention, an exemplary mechanism is described hereinafter.

Linear Drive Components

Figure 3:
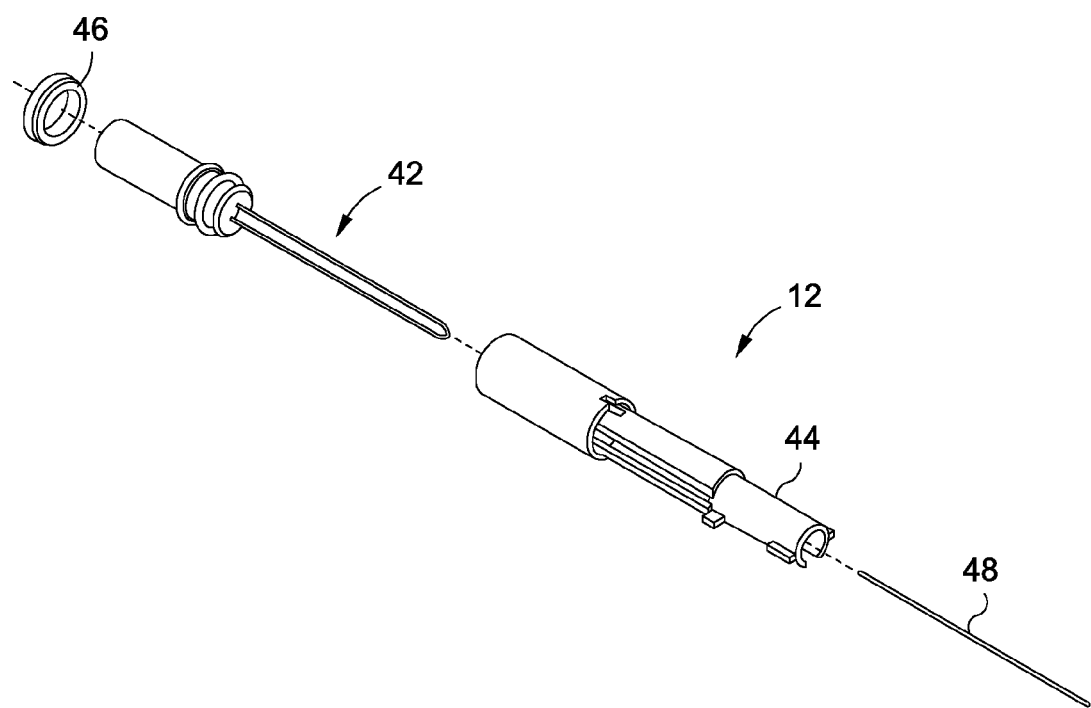
FIG. 3 is an exploded view of the linear drive components of the device shown in FIG. 1.
Figure 4:
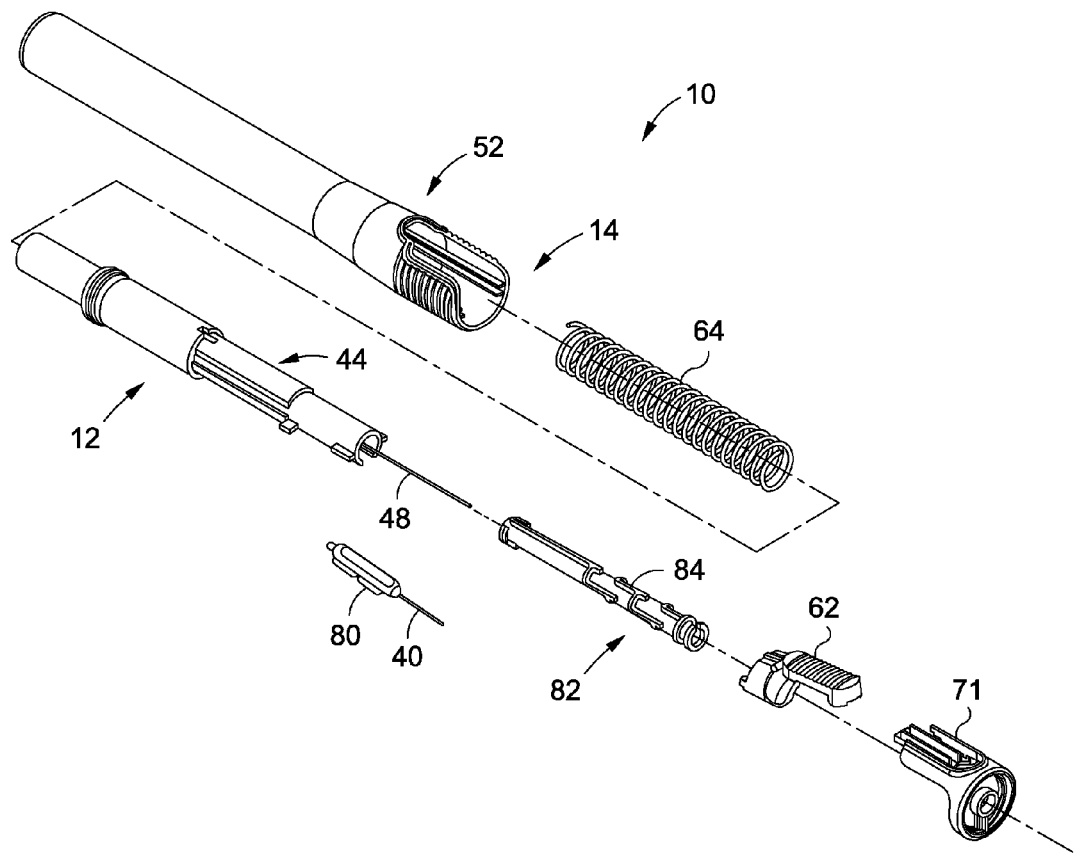
FIG. 4 is an exploded view of the rear drive assembly components of the device shown in FIG. 1.
Figure 5:
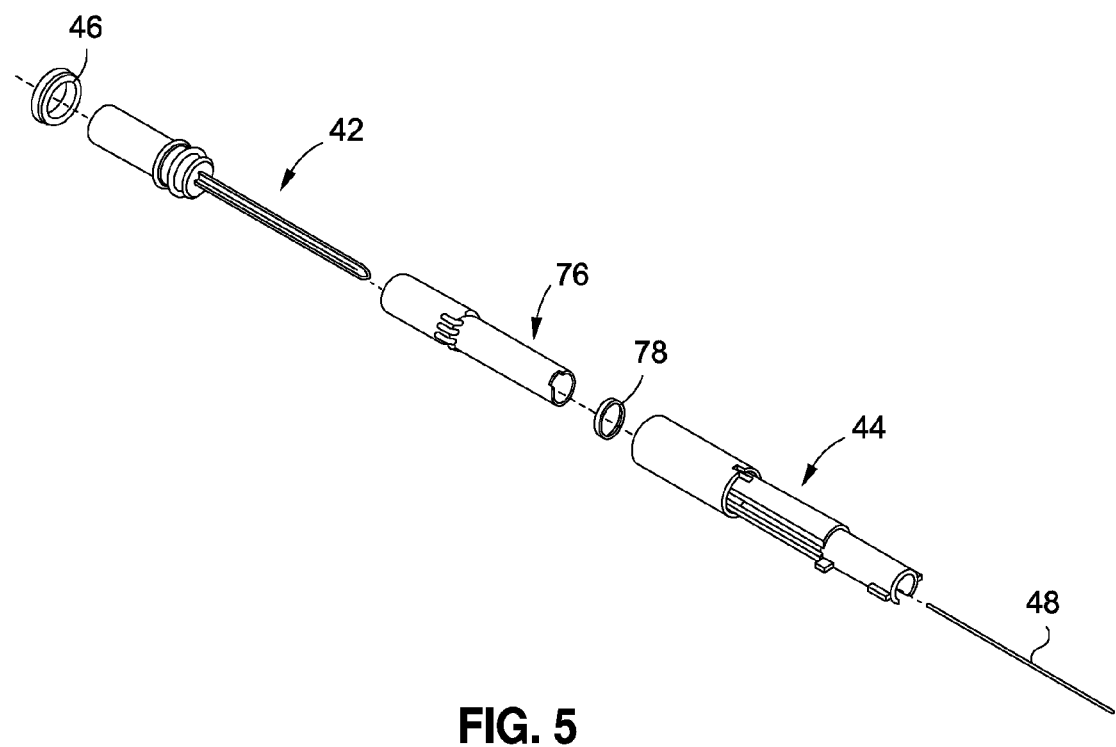
FIG. 5 is an exploded view of the drive rod assembly components of the device shown in FIG. 1.

Turning now to FIGS. 3-5, the present device 10 may include a drive rod assembly 12 housed within a rear drive assembly 14. The drive rod assembly 12 functions as a linear drive mechanism to force a plunger rod forward to cause ejection of implants. The drive rod assembly 12 may comprise a drive rod 42, a drive rod outer 44, a seal 46 and a plunger 48, fixed together and axially slidable within a rear body part 52 of the rear drive assembly 14, and otherwise relatively fixed thereto. The plunger 48 passes into the end of the needle/cannula 40 secured to distal end of the device 10 to cause ejection of implant segments 20 into the eye.

The device 10 may be actuated by the user pressing a release button 62, which drives the plunger 48 to push the implant segments 20 along the needle by means of a compression spring 64.

Compression Spring and Damping

The compression spring 64 is used to provide energy to drive the injection mechanism. The compression spring 64 may be stored in a compressed state in the device 10, and impinges on the rear body 52 and drive rod 42.

Damping may be used to control the speed at which the drive rod 42 moves under the compression spring action. The damping function may be achieved in any suitable manner. For example, in one embodiment, an enclosed air cavity is formed in the rear body 52. As the drive rod 42 moves forward, the volume of the air cavity then increases. A small hole in the rear body may be provided to allow air to be drawn into the cavity restricting the mechanism's speed. The hole size and compression spring characteristics may be structured such that the full travel of the drive rod assembly occurs in approximately 1.5 seconds.

Release Button

The release button 62, retained by a release button retainer 71, and functions as a catch to stop the drive rod assembly 12 from being pushed forward by the compression spring 64 prior to actuation. Features, for example, catch faces, on either side of the release button 62 engage with features on the drive rod outer 44. When the user presses on the release button 62, the release button 62 pivots and the catch faces move out of engagement. The catch faces and pivot position are such that the compression spring is compressed slightly as the release button 62 is pivoted resulting in a release button actuation force felt by the user.

The release button 62 is prevented from pivoting when a cap 72 is on, for example, by a suitable feature, for example, a tab feature on the cap 72. This prevents the device 10 from being inadvertently actuated, for example when the device 10 is being transported in its packaging.

Needle Rotation

A helix sleeve 76 is housed in drive rod outer 44 and can be rotated about a cylindrical axis of the device 10. Two tangs of a torsion spring 78 are located on the helix sleeve 76 and drive rod outer 44 such that the torsion spring 78 applies a restoring torque as the helix sleeve 76 is rotated.

A needle hub rear 82 is provided which fixes to needle 40. The needle hub rear 82 may include features, for example, a pair of stepped rib features 84, positioned such that they impinge on the helical surface of ribs on helix sleeve 76 causing the helix sleeve 76 to rotate as the helix sleeve 76 and drive rod outer 44 move forward. This relative rotation causes the torsion spring 78 and helix sleeve 76 to apply a torque between the drive rod outer 44 and the needle hub rear 82.

Rotating Needle Components

The needle 40 secured to needle hub 80, and needle hub rear 82 may be fixed together and can be rotated about the cylindrical axis of the parts and are fixed in the axial direction.

In addition to the features on the helix sleeve 76 as previously described, the pair of stepped rib features 84 on the needle hub rear 82 may be provided to be acted on by a pair of cooperating peg features on the drive rod outer 44.

The peg features, or other structure may be provided to act as a stop to prevent the needle hub rear 82 from rotating under the torque applied by the torsion spring 78 and helix sleeve 76.

In the shown embodiment, the needle 40 is rotated in increments of 90 degrees between each ejection of an implant segment. For example, when the peg features pass trailing corners on the stepped ribs 84, the needle components are rotated 90° under to action of the torsion spring 78, stopping when the peg features come into contact again with the stepped rib 84.

The 90° rotation occurs in a fraction of the time it takes the linearly driven parts of the mechanism to be driven between steps and therefore the needle has an intermittent 90° step rotation. In one aspect of the invention, the rotator mechanism is configured to rotate the cannula in the stepwise manner to complete a 360 degree rotation cycle. This may facilitate removal of the cannula from the eye at the end of treatment.

Other Functions

Dose Retention

Figure 6A:
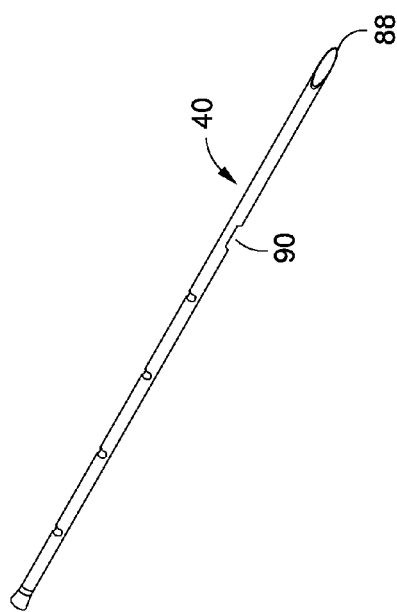
FIGS. 6A and 6B show a cannula useful in the invention having a curved distal end with a radius of curvature of about 50 degrees (R 50).
Figure 6B:
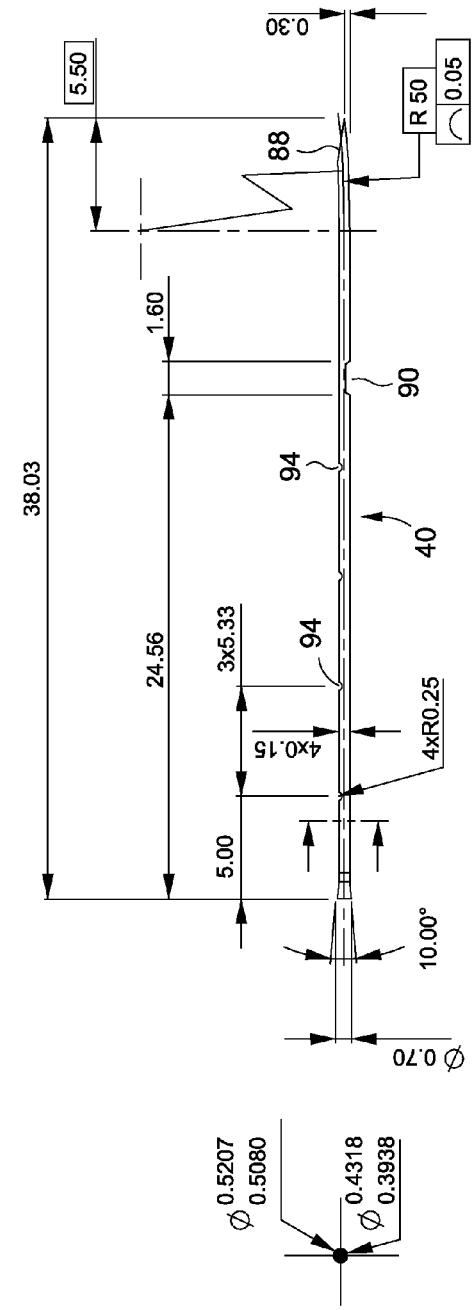

Turning briefly to FIGS. 2, 6A and 6B, the implant segments 20 may be kept in the device 10 prior to being ejected from the tip 88 of needle 40. This may be achieved by any number of ways, for example, having a hole 90 through the sidewall of the needle 40 which allows a flexible finger feature on the needle hub to form a stop within the needle 40. Before the device 10 is actuated, there is sufficient space between the needle hub stop finger feature and plunger for a 4-dose segment stack. The doses push past the flexible finger feature when they are pushed by the plunger when the device is actuated. When the cap 72 is on the device 10, for example in storage, a rib feature on the cap may prevent the finger feature from flexing such that that the dose segments are more securely held in the needle 40.

Dose Presence Confirmation

Means to confirm the correct number of dose segments are loaded into the device, both in manufacturing and immediately prior to use by the user, may be provided. This may be achieved by having the same number of holes 94 in the needle 40 as segment placed such that a segment will be visible through each hole 94 if the correct number of segments is present in the device.

After use and when the needle has been withdrawn from the patient's eye, the plunger 48 will be visible projecting from the tip of the needle 40. This allows the user to confirm that all of the segments have been ejected from the device.

Needle Backstop for 2 and 3 Segment Variant Devices

It is possible to use the device to inject fewer segments than the 4 shown in FIG. 2, simply by inserting fewer implants into the device in manufacturing. Note however that, in this case, the position of the segments in the needle may not be well controlled in the needle and the visibility of the segments would not give reliable indication of the presence correct number of segments.

To avoid this issue, a backstop part may be included on the 2 and 3 segment variant device assemblies. The backstop part is fixed to the needle and has a flexible finger feature with passes through a hole in the sidewall of the needle. There is sufficient space between the backstop and needle hub finger features for the 2 or 3 dose segment stack. The flexible finger of the backstop does not allow the dose segments to move past it towards the plunger but allows the plunger past to eject the segments when the device is actuated.

Injection Complete Indicator

Turning back now to FIGS. 1 and 2, in the embodiment shown, a front body 90 on the distal portion of the device 10 may be transparent such that the drive rod outer 44 moves into view through the front body at the end of the linear stroke when the device is actuated. Suitable means, for example, an embossed line on the transparent front body, may be provided to provide a more accurate indication that the device has ejected all of the dose segments.

While this invention has been described with respect to various specific examples and embodiments, it is to be understood that the invention is not limited thereto and that it can be variously practiced within the scope of the invention.

What is claimed is:

1. An assembly for implanting ocular implants into a mammalian eye, the assembly comprising:
   a rear body;
   a cannula having a longitudinal axis and a curved distal end;
   implant segments disposed in the cannula;
   an injector mechanism coupled to the cannula for linearly moving the implant segments in the cannula toward the curved distal end; and
   a rotator mechanism for rotating the cannula about the longitudinal axis thereof and relative to the rear body.

2. The assembly of claim 1 wherein the injector mechanism comprises a drive rod assembly and a compression spring coupled thereto.

3. The assembly of claim 1 wherein the injector mechanism comprises a drive rod assembly, a compression spring for driving forward the drive rod assembly, and a plunger having a distal end movable in the cannula.

4. The assembly of claim 1 wherein the rotator mechanism is structured to rotate the curved distal end of the cannula in a stepwise manner.

5. The assembly of claim 1 wherein the rotator mechanism comprises a rotatable sleeve having helical ribs.

6. The assembly of claim 1 wherein the rotator mechanism comprises a rotatable sleeve having helical ribs and a torsion spring for applying a restoring force.

7. The assembly of claim 1 wherein the curved distal end of the cannula has a distal tip offset between about 0.1 mm to about 1.0 mm.

8. The assembly of claim 1 wherein the curved distal end of the cannula has a distal tip offset about 0.2 mm.

9. The assembly of claim 1 wherein the curved distal end of the cannula has a distal tip offset about 0.3 mm.

10. The assembly of claim 1 wherein the curved distal end of the cannula has a distal tip offset about 0.5 mm.

11. The assembly of claim 1 wherein the rotator mechanism is configured to rotate the cannula 360 degrees.

12. An assembly for implanting ocular implants into a mammalian eye, the assembly comprising:
    a rear body;
    a cannula having a longitudinal axis and a curved distal end;
    implant segments disposed in the cannula;
    an injector mechanism coupled to the cannula linearly moving the implant segments in the cannula toward the curved distal end; and
    a rotator mechanism capable of rotating the cannula relative to the rear body and in a stepwise manner such that a distal tip of the cannula becomes offset relative to a position of the distal tip prior to each rotation step.

13. The assembly of claim 12 wherein the implant segments comprise a polymeric drug delivery system.

14. The assembly of claim 12 wherein the implant segments comprise between about two and about six implant segments.

15. The assembly of claim 12 wherein the implant segments comprise four implant segments.

16. The assembly of claim 12 wherein the rotator mechanism is configured to rotate the cannula in the stepwise manner to complete a 360 degree rotation cycle.

\* \* \* \* \*